United States Patent [19]
Van Voorhis

[11] Patent Number: 5,830,192
[45] Date of Patent: Nov. 3, 1998

[54] IRRIGATION SLEEVE FOR PHACOEMULSIFICATION APPARATUS

[75] Inventor: David Van Voorhis, Fontana, Calif.

[73] Assignee: Staar Surgical Company, Inc., Monrovia, Calif.

[21] Appl. No.: 762,123

[22] Filed: Dec. 9, 1996

[51] Int. Cl.⁶ .................................................. A61M 25/00
[52] U.S. Cl. ............................................ 604/280; 604/22
[58] Field of Search .......................... 604/22, 264, 280, 604/281, 282, 167–180

[56] References Cited

U.S. PATENT DOCUMENTS

| | | | |
|---|---|---|---|
| 4,643,717 | 2/1987 | Cook et al. | 604/22 |
| 4,787,889 | 11/1988 | Steppe et al. | 604/22 |
| 4,808,154 | 2/1989 | Freeman | 604/22 |
| 5,084,009 | 1/1992 | Mackool | 604/22 |
| 5,123,903 | 6/1992 | Quaid et al. | 604/22 |
| 5,151,084 | 9/1992 | Khek | 604/22 |
| 5,188,589 | 2/1993 | Wypych et al. | 604/22 |
| 5,199,943 | 4/1993 | Wypych | 604/22 |
| 5,286,256 | 2/1994 | Mackool | 604/22 |
| 5,421,829 | 6/1995 | Olichney et al. | 604/22 |
| 5,505,693 | 4/1996 | Mackool | 604/22 |
| 5,676,649 | 10/1997 | Boukhny | 604/22 |

*Primary Examiner*—Manuel Mendez
*Attorney, Agent, or Firm*—Klima & Pezzlo, P.C.

[57] ABSTRACT

An irrigation sleeve for use with a hand held portion of a phacoemulsification apparatus. The irrigation sleeve includes a base portion configured for removable attachment to the hand held portion of the phacoemulsification apparatus, an extending portion connected to the base portion and a passageway extending through the base and extending portions. Preferably, the irrigation sleeve is substantially rigid and at least the extending portion is made from a plastic material selected from the group consisting of polysulfone, polycarbonate, polyimide, and polyetherimide.

21 Claims, 5 Drawing Sheets

IRRIGATION SLEEVE FOR PHACOEMULSIFICATION APPARATUS

FIELD OF THE INVENTION

This invention relates to surgical instruments, and more particularly, to improved irrigation sleeves for use with phacoemulsification apparatus.

BACKGROUND OF THE INVENTION

When the natural lens of the eye no longer functions well, it may be removed and replaced with, for example, a deformable intraocular lens. Today, the natural lens of the eye may be removed through a relatively small incision in the eye with the use of phacoemulsification, a process in which the natural lens is disintegrated by the concentrated application of high frequency, low amplitude vibrations via a phacoemulsification needle.

The conventional phacoemulsification apparatus used to remove the natural lens of the eye has a hand held portion which includes an ultrasonic horn disposed within a cylindrical irrigation head. The distal end of a through bore in the horn is threaded to receive the threaded proximal end of a replaceable titanium phacoemulsification needle. The phacoemulsification needle is provided with a hollow cutting tip. The distal end of the irrigation head is externally threaded to receive the threaded proximal end of a replaceable irrigation sleeve. When the cutting tip and irrigation sleeve are installed on the hand held portion of the phacoemulsification apparatus, an irrigation sleeve conduit is formed by the concentric arrangement of the outer surface of the cutting tip and the inner surface of the irrigation sleeve.

During surgery, the cutting tip and the irrigation sleeve are introduced to the capsule of the eye through a three to five millimeter incision in the outer tissue of the eye. The hand held portion is maneuvered by the surgeon so that the distal end of the cutting tip is brought into contact with the natural lens. The cutting tip is then ultrasonically vibrated to fragment the natural lens. The resultant natural lens fragments combine with irrigation solution to form an emulsion. A vacuum provided to the through bore of the ultrasonic horn and communicated through the hollow cutting tip aspirates the emulsified lens from the eye.

Throughout the surgical removal of the lens, an irrigating fluid is pumped to the irrigation head, through the irrigation sleeve conduit and into the eye. The irrigating fluid pressurizes and inflates the eye and thus counteracts the tendency of the eye to collapse due to the release of internal pressure through the surgical incision and the removal of the emulsified lens by vacuum. Further, the irrigating fluid protects the delicate tissues of the eye from the heat created by the ultrasonic vibration of the cutting tip, and also provides a suspending fluid for aspirating the emulsified lens.

Thus, the supply of irrigating fluid to the eye is of crucial importance to the use of phacoemulsification to remove the natural lens. Indeed, a patient's eyesight is threatened when the flow of irrigation fluid is impeded, or worse, fully blocked during the lens removal procedure. The most common cause of eye injury associated with an interruption in the delivery of irrigation fluid occurs when the force of the ocular incision against the irrigation sleeve causes the inner surface of the extending portion of the irrigation sleeve to contact the outer surface of the cutting tip, thus occluding the irrigation sleeve conduit.

To prevent the compression of the irrigation sleeve and the resultant impedance to the flow of irrigation fluid through the irrigation sleeve conduit, it has been proposed to slightly enlarge the incision in the ocular tissue to better accommodate the irrigation sleeve. However, enlarging the ocular incision allows irrigating fluid to rapidly escape from space between the surface of the incision and the outer surface of the irrigation sleeve. The irrigating fluid is thereby prevented from maintaining the eye in a pressurized and inflated condition.

Background information pertaining to phacoemulsification devices including irrigation sleeves is disclosed in U.S. Pat. No. 4,787,889 to Steppe et al., U.S. Pat. No. 4,808,154 to Freeman, U.S. Pat. No. 5,084,009 to Mackool, U.S. Pat. No. 5,151,084 to Khak, 5,188,589 to Wypych et al., and U.S. Pat. No. 5,505,693 to Mackool. These patent references are incorporated herein by reference to provide the context and environmental use of the irrigation sleeves according to the present invention.

SUMMARY OF THE INVENTION

Accordingly, it is a first object of the present invention to provide an irrigation sleeve which resists compression.

It is a second object of the present invention to provide an irrigation sleeve which does not leak at the connection to the irrigation head.

It is a third object at the present invention to provide an irrigation sleeve which decreases the loss of irrigation fluid at the interface of the irrigation sleeve and the ocular incision.

It is a fourth object of the present invention to provide an irrigation sleeve which resists loosening during phacoemulsification.

It is a fifth object of the present invention to provide an irrigation sleeve which dampens ultrasonic vibration transmitted through the irrigation sleeve.

It is a sixth object of the present invention to provide an irrigation sleeve which decreases the amount of cavitation in the irrigating fluid.

It is a seventh object of the present invention to provide an irrigation sleeve which allows for increased levels of ultrasonic energy to be applied to the cutting tip.

It is an eighth object of the present invention to provide an irrigation sleeve which decreases turbulence of the irrigating fluid.

It is a ninth object of the present invention to provide an irrigation sleeve with improved cutting tip maneuverability.

It is a tenth object of the present invention to provide an irrigation sleeve which includes a wall portion made of a substantially rigid material and a coating portion made of a soft and resilient material.

It is an eleventh object of the present invention to provide an irrigation sleeve which includes a base portion, an intermediate portion, an extending portion, and a longitudinal passageway.

It is a twelfth object of the present invention to provide an irrigation sleeve which includes a multi-piece irrigation sleeve which is assembled immediately prior to use and allows for different base portion, intermediate portion and extending portion combinations.

It is a thirteenth object of the present invention to provide an irrigation sleeve which includes a base portion and an integral intermediate portion made of a substantially rigid material coated with a soft and resilient material, and an extending portion made of a substantially rigid material coated with a soft and resilient material.

It is a fourteenth object of the present invention to provide an irrigation sleeve which includes a base portion and an integral intermediate portion made of a soft and resilient material connected to an extending portion made of a substantially rigid material.

It is a fifteenth object of the present invention to provide an irrigation sleeve having a base portion and an integral intermediate portion made of silicone and an extending portion made of polysulfone.

The present invention is directed to an improved phacoemulsification apparatus, in particular to an improved irrigation sleeve.

The improved irrigation sleeve according to the present invention is arranged to prevent compression or restriction of the irrigation sleeve conduit, and/or to improve the seal between the irrigation sleeve and the irrigation head.

One preferred embodiment of the irrigation sleeve according to the present invention utilizes a base portion made of a soft and resilient material connected to an extending portion made of a substantially rigid material. For example, a molded silicone base is connected to a polysulfone extending portion. The resilient nature of the silicone base provides a leak-proof seal with the irrigation head while the polysulfone extending portion significantly resists compression.

Another preferred embodiment of the irrigation sleeve according to the present invention utilizes a substantially rigid irrigation sleeve provided with a soft and resilient coating portion (e.g. internal threads only, or entire inner surface and/or outer surface).

When the extending portion of this preferred embodiment (utilizing a substantially rigid irrigation sleeve provided with a soft and resilient coating portion) of the irrigation sleeve of the present invention is placed within an ocular incision, the soft and resilient coating portion, for example, on a wall portion of the extending portion provides a gentle surface which conforms to the contour of the ocular incision to inhibit the loss of irrigation fluid therefrom. Also, the substantially rigid material of the wall portion of the extending portion prevents the compressive force of the ocular incision from deforming the extending portion such that the inner surface thereof contacts the outer surface of the cutting tip. Further, the combination of the substantially rigid material of the wall portion at the base portion, and the soft and resilient material of the coating portion on the wall portion of the base portion prevent leakage and/or loosening of the sleeve at the connection of the irrigation sleeve to the irrigation head.

DETAILED DESCRIPTION OF THE PREFERRED EMBODIMENTS

Figure 1:
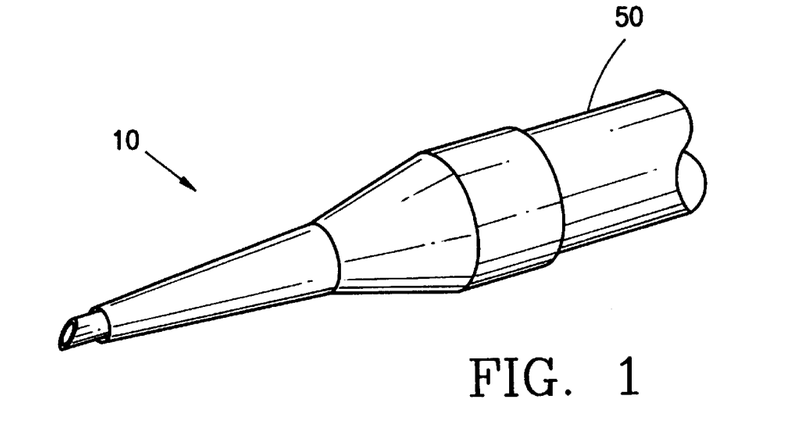
FIG. 1 is a perspective view of a first embodiment of an irrigation sleeve according to the present invention installed on the hand held portion of a conventional phacoemulsification apparatus.
Figure 2:
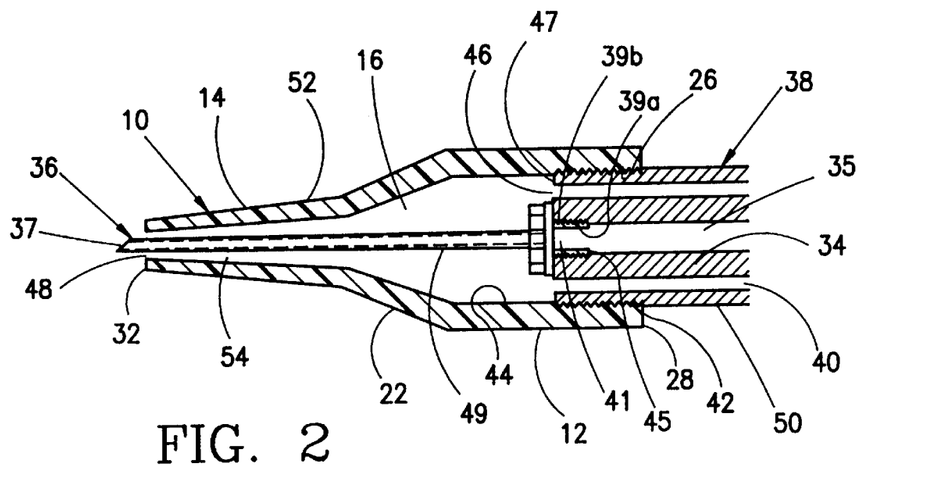
FIG. 2 is a longitudinal cross-sectional view of the assembly shown in FIG. 1.

FIGS. 1 and 2 show an irrigation sleeve 10 according to the present invention installed on the hand held portion 50 of a conventional phacoemulsification apparatus. The irrigation sleeve 10 is made of a substantially rigid plastic material resistant to deformation. Specifically, the irrigation sleeve 10 is made of a substantially rigid plastic material that resists inwardly directed compression from the eye incision that would tend to pinch the irrigation sleeve against the needle and restrict the flow of irrigation fluid during use. Preferred plastic materials include polyolefins, in particular polyethylene and polypropylene. However, these materials have melting points close to the temperature and pressure required for autoclaving. Thus, polyolefins are particularly suitable for one time use (i.e. disposable) applications. More preferred plastic materials including polysulfone, polycarbonate, polyimide, and polyetherimide, provide irrigation sleeves that can be sterilized by autoclaving.

Importantly, the irrigation sleeve 10 is designed or configured to tightly seal with the hand held portion 50 of the phacoemulsification apparatus, even though the irrigation sleeve 10 is made of substantially rigid plastic material compared to conventional silicone irrigation sleeves, and without a separate sealing component (e.g. "O" ring). For example, the internal threads of the irrigation sleeve 10 can be made slightly undersized, or the thread design can be modified to cause one or more threads to undergo resilient or permanent deformation to provide a sealing function with the external threads of the handheld portion of the phacoemulsification apparatus. Alternatively, an additional internal integral seal (e.g. ring) can be molded into the irrigation sleeve 10 to cause sealing engagement with the hand held portion of the phacoemulsification apparatus. While providing a one-piece molded design of the irrigation sleeve. Further, an adhesive and/or sealing composition (e.g. silicone sealant) can be provided (e.g. coated) on the integral threads of the irrigation sleeve to enhance sealing with the external threads of the hand held portion of the phacoemulsification apparatus.

The hand held portion 50 of the conventional phacoemulsification apparatus includes an ultrasonic horn 34 disposed within a cylindrical irrigation head 38. The distal end 41 of a through bore 35 in horn 34 includes an internally threaded portion 39a which engages the externally threaded portion 39b of the proximal end 45 of a replaceable hollow cutting tip 36 (i.e. phacoemulsification needle).

The distal end 47 of irrigation head 38 is configured for receiving the proximal end 28 of irrigation sleeve 10. In the preferred embodiment shown, the inner surface 44 of the base portion 12 of irrigation sleeve 10 includes an internally threaded portion 26 which engages an externally threaded portion 42 of the distal end 47 of irrigation head 38. Other arrangements may be used for attaching irrigation sleeve 10 to irrigation head 38. For example, base portion 12 may be attached to irrigation head 38 by a compression fit.

In the embodiment shown in FIGS. 1 and 2, the outer surface 52 of irrigation sleeve 10 along base portion 12 is cylindrically shaped. However, outer surface 52 may be other shapes. For example, outer surface 52 may define a substantially conical shape. Further, the transverse cross-sectional shape of outer surface 52 is smooth and circular. However, the transverse cross-sectional shape of outer surface 52 of base portion 12 may define other shapes and textures. For example, the transverse cross-sectional shape of outer surface 52 of base portion 12 may define a hexagonal shape, or a knurled surface for mounting, by tool or by hands, respectfully, irrigation sleeve 10 onto irrigation head 38.

The base portion 12 of the irrigation sleeve 10 connects to an intermediate portion 22, and an extending portion 14 which extends towards, but terminates short of, the distal end of cutting tip 36. The outer surface 52 of the irrigation sleeve 10 at the intermediate portion 22 and extending portion 14 is conical. However, the outer surface 52 may define a series of stepped components which define other shapes. For example, outer surface 52 may be cylindrically shaped along intermediate portion 22 and conically shaped along extending portion 14. Further, base portion 12 may transition directly to extending portion 14 with no intermediate portion 22 therebetween.

Figure 3:
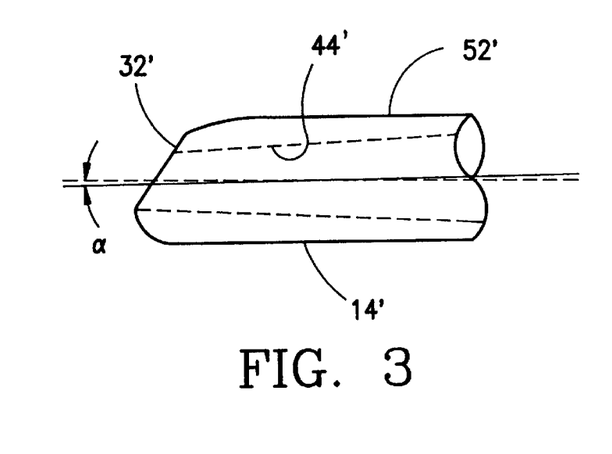
FIG. 3 is a broken away partial side view of an extending portion of an irrigation sleeve according to the present invention.

The inner surface 44 of base portion 12, intermediate portion 22, and extending portion 14 forms a passageway 16 along the longitudinal axis of irrigation sleeve 10. In the embodiment shown in FIGS. 1–2, the longitudinal cross-sectional of inner surface 44 substantially parallels the shape of the outer surface 52 of irrigation sleeve 10. However, the base portion 12, intermediate portion 22, and extending portion 14 may be configured so that the longitudinal cross-section of inner surface 44 defines a variety of different shaped passageways along the longitudinal axis of irrigation sleeve 10. For example, in an alternative embodiment shown in FIG. 3, a portion of the longitudinal cross-section of inner surface 44' within extending portion 14' may taper inwardly, and define a section of a cone having an angle $\alpha$, (e.g. two (2) degrees) relative to the longitudinal axis of irrigation sleeve 10. The longitudinal cross-section of outer surface 52' of extending portion 14' may define a section of a cylinder, and may be oriented parallel to the longitudinal axis of the irrigation sleeve 10.

In the embodiment shown in FIGS. 1–2, the transverse cross-section of inner surface 44 defines a circle. However, the transverse cross-section of inner surface 44 may have other suitable shapes, including, for example, a polygonal shape, an elliptical shape or other shapes. Inner surface 44 may also be configured to include such features as rifling, texturing (e.g ridged or bumped), or other suitable configurations.

The concentric arrangement of the outer surface of the horn 34 and the inner surface of the irrigation head 38 forms an annular irrigation head conduit 40 as shown in FIG. 2. Annular irrigation head conduit 40 communicates to the entrance 46 of an irrigation sleeve conduit 54 formed by the outer surface of cutting tip 36 and the inner surface 44 of irrigation sleeve 10. In the embodiment shown in FIGS. 1 and 2, the cross-sectional area of conduit 54 decreases from entrance 46 to an exit 48 located at the distal end 32 of irrigation sleeve 10.

During surgery, extending portion 14 of irrigation sleeve 10 and cutting tip 36 are introduced to the capsule of the eye through a 0.5 to 5 millimeter (mm) incision in the outer tissue of the eye. Irrigating fluid is pumped through annular conduit 40 and irrigation sleeve conduit 54 into the surgical site from exit 48. When the cutting tip 36 is sufficiently proximal to the natural lens, the ultrasonic horn 34 is activated causing the ultrasonic vibration of the cutting tip 36 which emulsifies the natural lens. The remnants of the natural lens and the irrigation fluid in which the remnants of the lens are suspended are removed from the eye through the open distal end 37 of hollow cutting tip 36 by a vacuum provided to tip 36 via through bore 35 in ultrasonic horn 34.

Figure 4:
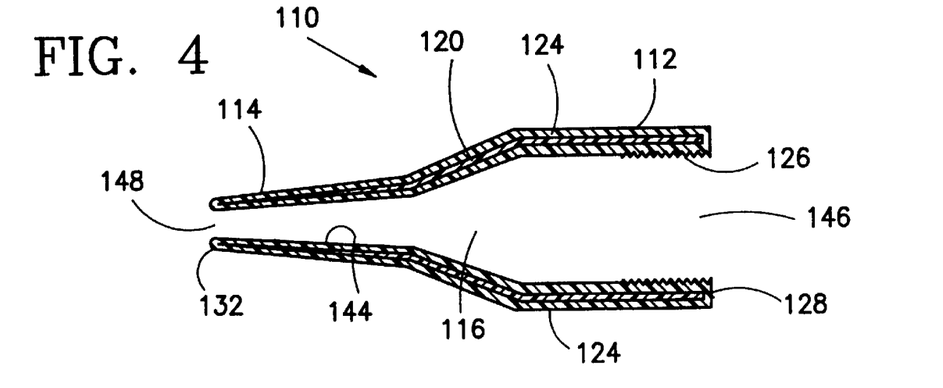
FIG. 4 is a detailed longitudinal cross-sectional view of a second embodiment of an irrigation sleeve according to the present invention.
Figure 5:
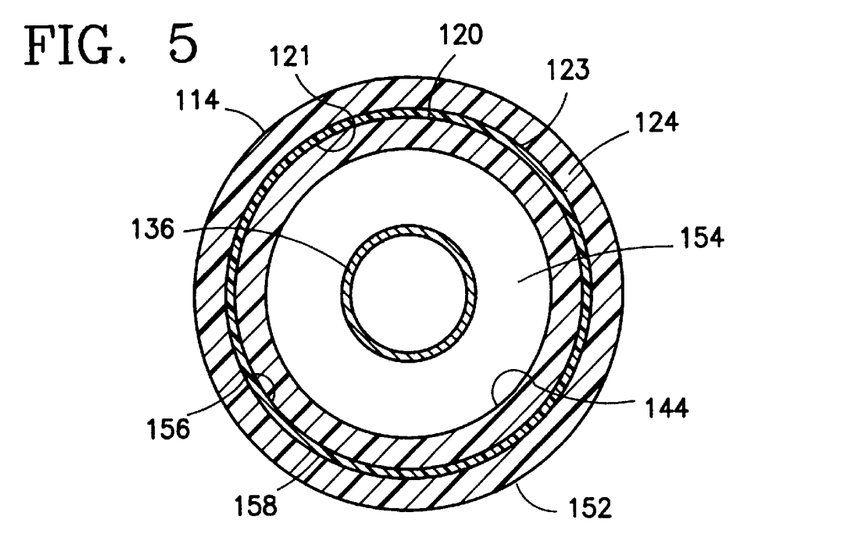
FIG. 5 is a detailed transverse cross-sectional view of the assembly as indicated in FIG. 1.

FIG. 4 shows a second embodiment of an irrigation sleeve 110. Irrigation sleeve 110 includes a wall portion 120 made of a substantially rigid material, for example polysulfone, and a coating portion 124 made of a soft and resilient material such as silicone. In the embodiment shown in FIG. 4, wall portion 120 is continuous and coating portion 124 is applied uniformly to wall portion 120.

The substantially rigid material of wall portion 120 prevents improper deformation of irrigation sleeve 110 and the soft and resilient material of coating portion 124 provides an improved surface for irrigation sleeve 110. For example, when the distal end 132 of extending portion 114 of irrigation sleeve 110 is inserted through the ocular incision, wall portion 120 prevents extending portion 114 from splaying, folding outwardly or wrinkling in an accordion-like manner along outer surface 152 of cutting tip 136. Further, coating portion 124 prevents the distal end 132 of extending portion 114 from cutting into or otherwise damaging the ocular tissues as the cutting tip 136 and irrigation sleeve 110 are passed therethrough.

While extending portion 114 of irrigation sleeve 110 is within the ocular incision, wall portion 120 prevents the inner surface 144 of extending portion 114 from contacting the outer surface of cutting tip 136. Wall portion 120 also prevents the radial and longitudinal expansion or contraction of the irrigation sleeve 110 due to forces such as fluctuation in fluid pressure at the irrigation head 138 or forces associated with the maneuvering of the irrigation sleeve 110 and cutting tip 136 within the eye. Because wall portion 120 resists deformation, in particular, those types of deformation which greatly disturb the inner surface 144 of irrigation sleeve 110, the flow of irrigation fluid to the eye is maintained in a substantially non-turbulent or laminar state.

Also, during insertion and while within the eye, coating portion 124 deforms according to the contour of the ocular incision to inhibit the loss of irrigation fluid at the interface between the outer surface 152 of the extending portion 114 of the irrigation sleeve 110 and the surface of the ocular incision. Further, coating portion 124 at the threaded portion 126 of base portion 112 engages the threaded surface of the irrigation head to prevent irrigating fluid from leaking at the connection therebetween and also to prevent the irrigation sleeve from becoming loose during phacoemulsification. Coating portion 124 dampens ultrasonic vibration transmitted form the inner surface 144 and the outer surface 152 of the cutting tip during phacoemulsification. Cavitation is thereby inhibited in the irrigating fluid thus improving the surgeon's view of the surgical site. Furthermore, because of the improved vibration damping, power may be increased to ultrasonic horn 134 and cutting tip 136 without damaging surrounding ocular tissue.

Preferably, materials of low thermal conductivity are used to make wall portion 120 and coating portion 124 so that the transfer of potentially damaging heat to the ocular tissue is inhibited. Those of ordinary skill in the art can readily select and employ suitable materials of low thermal conductivity. Further, embodiments of irrigation sleeve 110 having multiple internal boundaries provide improved vibration damping and heat insulating properties over embodiments including only one or no internal boundary.

Figure 6:
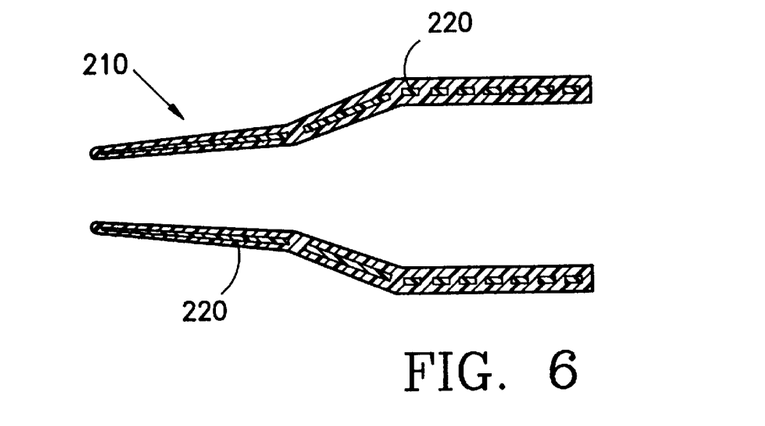
FIG. 6 is a detailed longitudinal cross-sectional view of a third embodiment of an irrigation sleeve according to the present invention.
Figure 7:
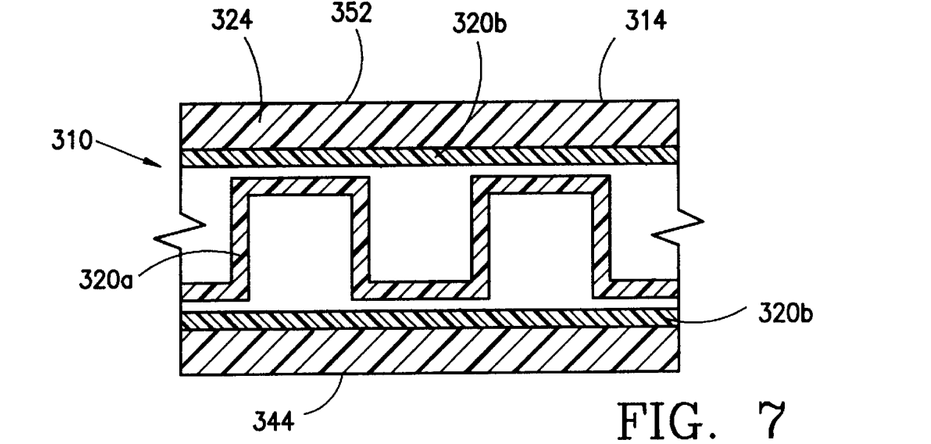
FIG. 7 is a broken away detailed cross-sectional view of a fourth embodiment of an irrigation sleeve according to the present invention.

An irrigation sleeve according to the present invention may also include a wall portion which is continuous or intermittent throughout any portion of the irrigation sleeve. For example, in a third alternative embodiment of the present invention shown in FIG. 6, wall portion 220 is made of a series of ribs 220. Multiple continuous wall portions may also be included in irrigation sleeve. For example, in the partial broken away view of extending portion 314 of the fourth alternative embodiment of irrigation sleeve 310 shown in FIG. 7, a central corrugated wall portion 320a is enveloped by outer wall portions 320b.

Coating portion 124 may also be configured to be continuous or intermittent on any portion of irrigation sleeve 110. For example, coating portion 124 might be provided only on the threaded surface 126 of base portion 112 and/or on the outer surface 152 of extending portion 114.

Figure 8:
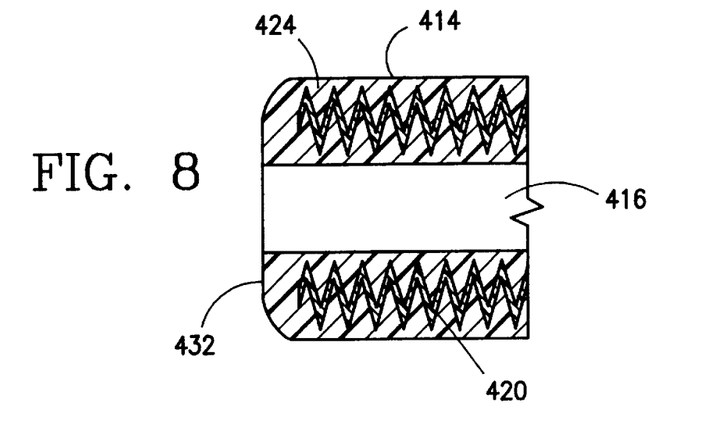
FIG. 8 is a broken away detailed cross-sectional view of a fifth embodiment of an irrigation sleeve according to the present invention.

Since coating portion 124 may be configured to provide a smooth inner surface 144 and a smooth outer surface 152, any feature included in wall portion 120 for improving the heat insulating properties, vibration dampening properties, or other measure of performance of irrigation sleeve 110 is prevented from posing a threat of injury to the tissue of the eye. For example, the longitudinal or transverse cross-section of wall portion 420 may define a relatively high frequency saw tooth wave, or other non-smooth profile, whereas the longitudinal and transverse cross-section on inner surface 444 and outer surface 452 may be smooth, as shown in FIG. 8.

In other alternative embodiments of the present invention, the soft and resilient material of coating portion 124 may be included in a structural component of irrigation sleeve 510 independently of the substantially rigid (i.e. resists deformation) material of wall portion 520. For example, in a sixth embodiment of the present invention shown in FIG. 9, base portion 512 and intermediate portion 522 are made of a soft and resilient material and extending portion 514 is made of a substantially rigid material.

In embodiments where a soft and resilient material is included as a structural component independent of the substantially rigid material of wall portion 20, a means for connecting components made of different materials is included in the irrigation sleeve. For example, in the embodiment shown in FIG. 9, the interior surface 544 of irrigation sleeve 510 at the distal end of intermediate portion 522 includes a circumferential channel 562 for receiving a flange 564 at the proximal end of extending portion 514. It is important to note that the connection formed by flange 564 and circumferential channel 562 further inhibits the transmission of ultrasonic vibration to extending portion 514 and thus provides an irrigation sleeve 510 with improved vibration dampening properties.

Figure 9:
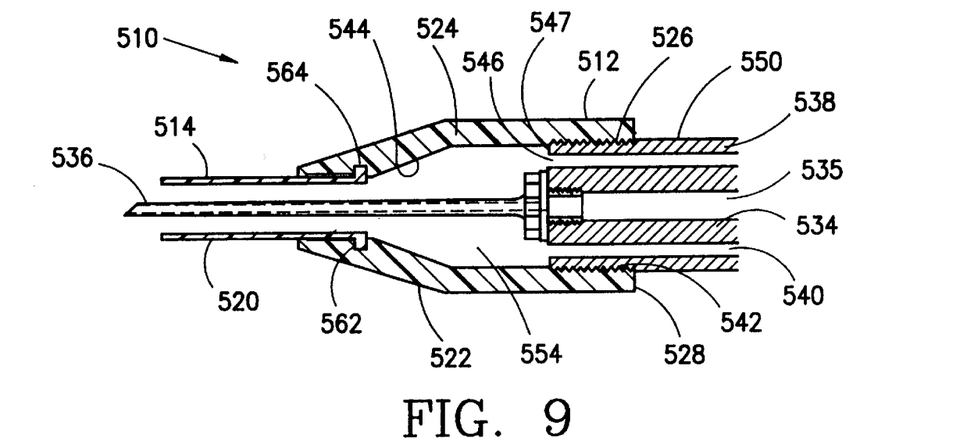
FIG. 9 is a detailed longitudinal cross-sectional view of a sixth embodiment of an irrigation sleeve according to the present invention installed on the hand held portion of a conventional phacoemulsification apparatus.
Figure 10:
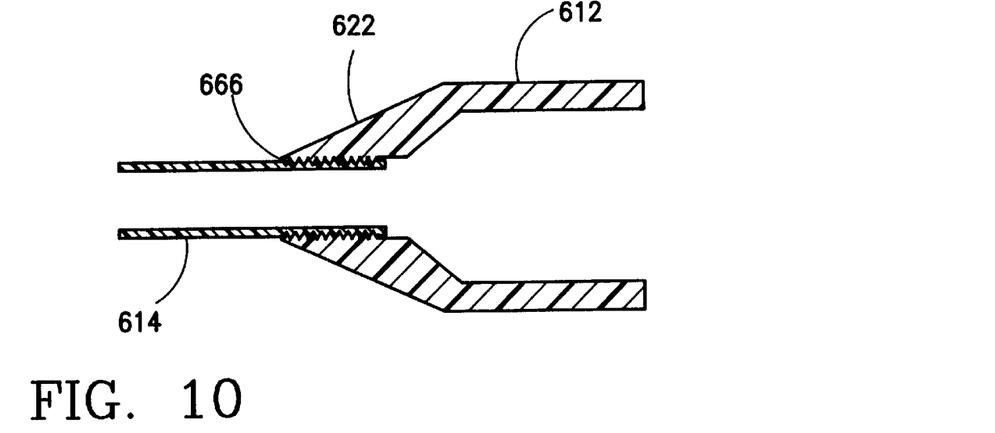
FIG. 10 is a detailed longitudinal cross-sectional view of a seventh embodiment of an irrigation sleeve according to the present invention.

A seventh embodiment of irrigation sleeve 610, shown in FIG. 10, is identical to that shown in FIG. 9 except that in the place of a flange and channel connection, extending portion 614 is connected to intermediate portion 622 by an adhesive 666. Alternatively, or in addition to other forms of connection, a sonic weld may be used to connect extending portion 614 to intermediate portion 622.

Figure 11:
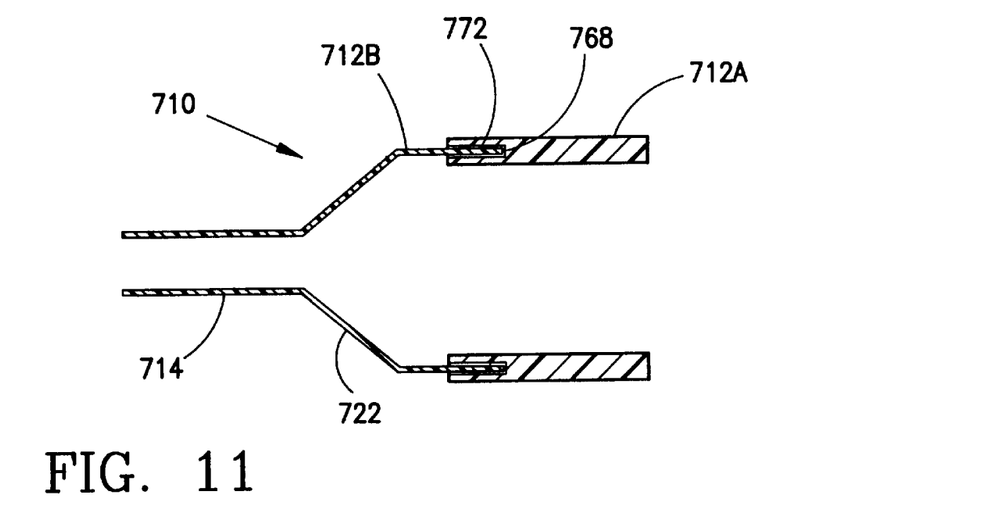
FIG. 11 is a detailed longitudinal cross-sectional view of a eighth embodiment of an irrigation sleeve according to the present invention.

An eighth embodiment of an irrigation sleeve 710 according to the present invention is shown in FIG. 11. Irrigation sleeve 710 includes a first base portion 712a, made of a soft and resilient material. First base portion 712a includes a groove 768 in the distal end thereof which is parallel to the longitudinal axis of the irrigation sleeve 710. Groove 768 is configured to receive a tongue 772 on the proximal end of a second base portion 712b. Second base portion 712b is made of a substantially rigid material. Second base portion 712b includes a conical shaped intermediate portion 722 and cylindrical extending portion 714, both also made of a substantially rigid material. Further, securing means, such as an adhesive or a barb and catch assembly, may be provided on tongue 772 for further securing second base portion 712b to first base portion 712a.

Figure 12:
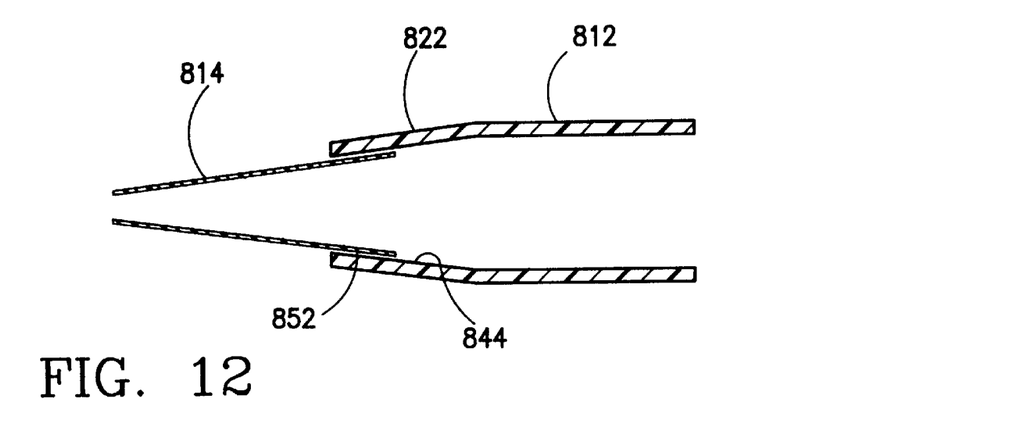
FIG. 12 is a detailed longitudinal cross-sectional view of an ninth embodiment of an irrigation sleeve according to the present invention.
Figure 13:
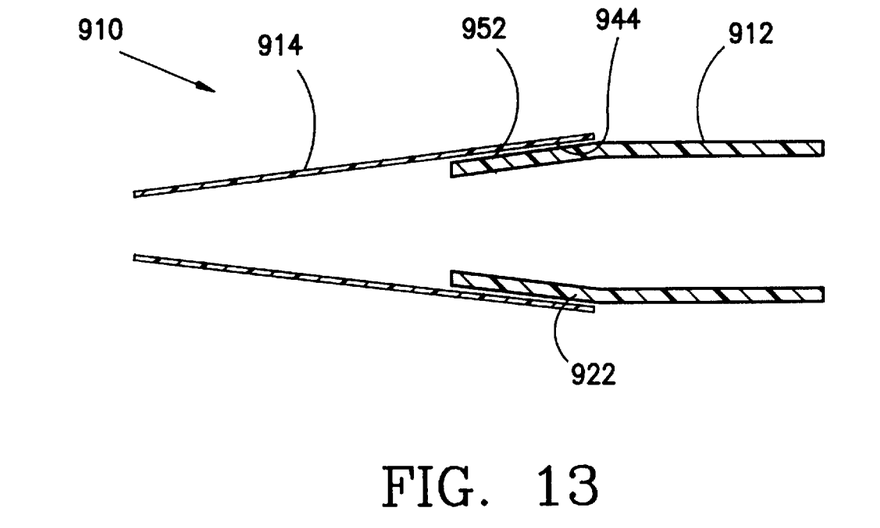
FIG. 13 is a detailed longitudinal cross-sectional view of a tenth embodiment of an irrigation sleeve according to the present invention.

A ninth embodiment of an irrigation sleeve 810 according to the present invention, shown in FIG. 12, includes a conical extending portion 814. The outer surface 852 at the proximal end of conical extending portion 814 engages the inner surface 844 of intermediate portion 822. In a tenth embodiment of irrigation sleeve 910 shown in FIG. 13, the inner surface 944 at the proximal end of conical extending portion 914 engages the outer surface 952 of intermediate portion 922. In the embodiments shown in FIGS. 12 and 13, extending portion 814 and 914, respectfully, is made of a substantially rigid material and base portion 812 (912) with integral intermediate portion 822 (922) is made of a soft and resilient material (e.g. a flexible sealing material). Also, a means of sealing, such as an adhesive, is included at the connection between extending portion 814 (914) and intermediate portion 822 (922).

During use, cutting tip 136 and extending portion 114 of the irrigation sleeve 110 are constantly maneuvered within the eye. Trauma to the ocular tissue is caused by the frictional contact between the small ocular incision and extending portion 114 during this movement. To alleviate or prevent some of this trauma and also to improve the maneuverability of the irrigation sleeve 110, irrigation sleeve 110 may be configured to move relative to cutting tip 136. In the embodiment shown in FIG. 9, relative rotational movement between extending portion 514 and intermediate portion 522 is provided by increasing the volume of channel 562, thus allowing flange 564 to "float" within channel 562.

Figure 14:
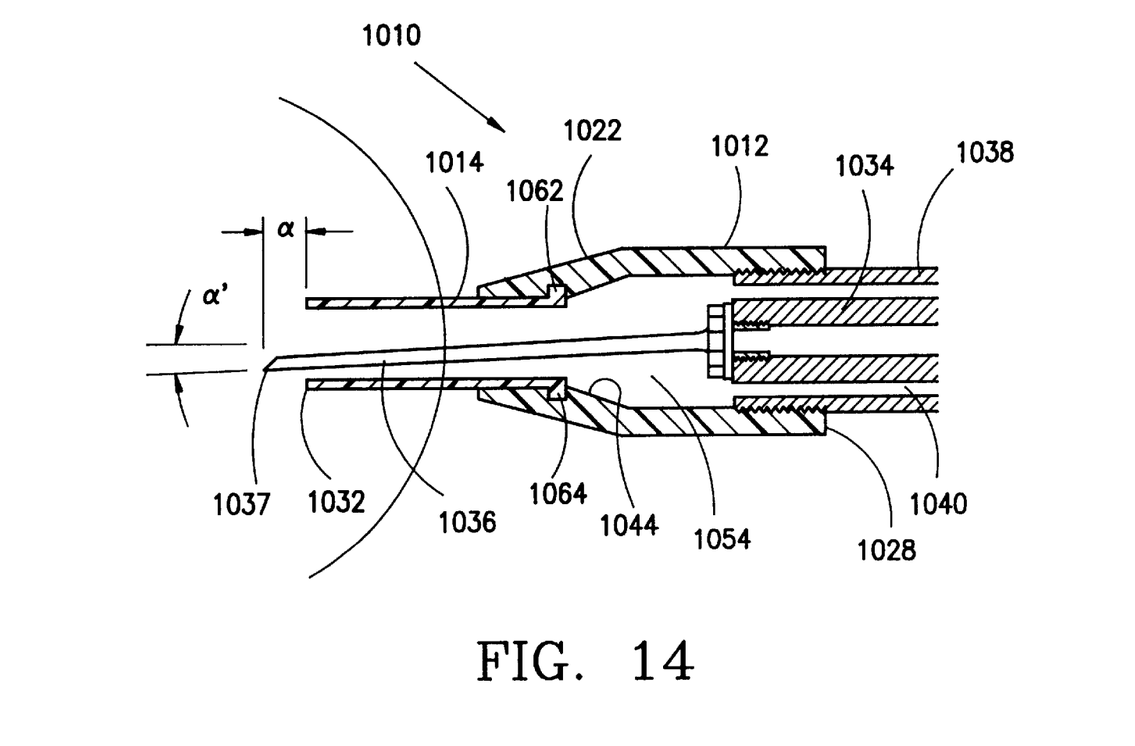
FIG. 14 is a detailed longitudinal cross-sectional view of the irrigation sleeve shown in FIG. 9 installed on the hand held portion of a conventional phacoemulsification apparatus.

Maneuverability of cutting tip 136 may be further improved by the inclusion of means for allowing a predetermined amount of relative movement, or "play", between extending portion 114 and the rest of irrigation sleeve 110. For example, as shown in FIG. 14, the soft and resilient material of base portion 1012 and intermediate portion 1022 may be configured to elastically deform to create an angle, $\alpha'$, between the longitudinal axis of the cutting tip 1036 and the normally collinear longitudinal axis of the extending portion 1014. Further, intermediate portion 1022 may be configured to elastically deform to create a change in distance, d, between the distal end 1037 of the cutting tip 1036 and the distal end 1032 of the irrigation sleeve 1010.

Further, the irrigation sleeve 1010 shown in FIG. 14 may be configured as part of a kit. During use of the kit in surgery, the surgeon chooses various combination of kit components to be connected in order to achieve desired characteristics of irrigation sleeve 1010. For example, a kit including a base portion 1012 with an integral intermediate portion 1022 may include separate extending portions 1014 of various diameters and lengths. After selecting desired components, the surgeon connects extending portion 1014 to base portion 1012 by placing the distal end of extending portion 1014 at the proximal end 1028 of passageway 1016. Extending portion 1014 is then pushed through base portion 1012 until the flange 1064 at the proximal end of the extending portion 1014 engages channel 1062 in intermediate portion 1022.

I claim:

1. An irrigation sleeve for use with a hand held portion of a phacoemulsification apparatus, said irrigation sleeve comprising:

an irrigation sleeve base portion configured for removable attachment to the hand held portion of the phacoemulsification apparatus;

an irrigation sleeve extending portion connected to said base portion;

a passageway extending through said base and extending portions;

wherein said irrigation sleeve includes an inner wall portion made of a substantially rigid material and an outer coating portion made of a soft and resilient material.

2. An irrigation sleeve according to claim 1, wherein said inner wall portion is made of polysulfone and said outer coating portion is made of silicone.

3. An irrigation sleeve according to claim 1, wherein said inner wall portion is continuous and said outer coating portion is applied uniformly to said wall portion.

4. An irrigation sleeve according to claim 1, wherein said inner wall portion is intermittent.

5. An irrigation sleeve according to claim 1, wherein said inner wall portion is provided only in said extending portion.

6. An irrigation sleeve according to claim 1, wherein said outer coating portion is intermittent.

7. An irrigation sleeve according to claim 1, wherein said outer coating portion is provided only on an outer surface of said extending portion.

8. An irrigation sleeve according to claim 1, wherein said outer coating portion is provided along the entire length of the irrigation sleeve.

9. An irrigation sleeve according to claim 1, wherein said soft and resilient material of said outer coating portion is a structural component independent of said substantially rigid material of said wall portion.

10. An irrigation sleeve according to claim 1, wherein said extending portion includes a substantially rigid tip portion and a substantially soft and resilient portion connected to said tip portion.

11. An irrigation sleeve according to claim 1, wherein said inner wall portion defines an inner layer, and said outer coating portion defines a separate outer layer connected to said inner layer.

12. An irrigation sleeve according to claim 11, including an inner coating portion made of a soft and resilient material, said inner coating portion connected to and located on an inner side of said inner wall portion.

13. An irrigation sleeve for use with a hand held portion of a phacoemulsification apparatus, said irrigation sleeve comprising:

an irrigation sleeve base portion configured for removable attachment to the hand held portion of the phacoemulsification apparatus;

an irrigation sleeve extending portion connected to said base portion, said extending portion including an outer layer made of a soft and resilient material and an inner stiffener made of a substantially rigid material for reinforcing said outer layer;

a passageway extending through said base and extending portions.

14. An irrigation sleeve according to claim 13, wherein said inner stiffener is made of polysulfone.

15. An irrigation sleeve according to claim 14, wherein said inner stiffener is a separate layer.

16. An irrigation sleeve according to claim 15, wherein said inner stiffener is an independent component of said irrigation sleeve.

17. An irrigation sleeve according to claim 15, wherein said inner stiffener is tubular shaped.

18. An irrigation sleeve for use with a hand held portion of a phacoemulsification apparatus, said irrigation sleeve comprising:

an outer irrigation sleeve made of a soft and resilient material;

an inner stiffener connected to and located inside said outer irrigation sleeve for reinforcing said irrigation sleeve to prevent collapsing of said outer irrigation sleeve and restriction of flow therethrough.

19. An irrigation sleeve according to claim 18, wherein said inner stiffener is a tubular shaped inner stiffener.

20. An irrigation sleeve according to claim 18, wherein said inner stiffener is held fixed relative to said outer irrigation sleeve by said outer irrigation sleeve.

21. An irrigation sleeve according to claim 18, wherein said outer irrigation sleeve is tubular shaped, and said inner stiffener is tubular shaped.

* * * * *